United States Patent
Hunter et al.

(10) Patent No.: US 6,441,042 B1
(45) Date of Patent: Aug. 27, 2002

(54) HYDROXAMIC ACID DERIVATIVES AS ANTIBACTERIALS

(75) Inventors: Michael George Hunter; Raymond Paul Beckett; John Martin Clements; Mark Whittaker; Zoe Marie Spavold, all of Oxford (GB)

(73) Assignee: British Biotech Pharmaceuticals Limited, Oxford (GB)

(*) Notice: Subject to any disclaimer, the term of this patent is extended or adjusted under 35 U.S.C. 154(b) by 0 days.

(21) Appl. No.: 09/700,424

(22) PCT Filed: May 14, 1999

(86) PCT No.: PCT/GB99/01541

§ 371 (c)(1),
(2), (4) Date: Nov. 15, 2000

(87) PCT Pub. No.: WO99/59568

PCT Pub. Date: Nov. 25, 1999

(30) Foreign Application Priority Data

May 16, 1998 (GB) ............................................... 9810464

(51) Int. Cl.[7] ............................................... A61K 31/19
(52) U.S. Cl. ............................................... 514/575
(58) Field of Search ............................................... 514/575

(56) References Cited

U.S. PATENT DOCUMENTS 5,532,265 A 7/1996 Gijbels et al.
5,962,529 A * 10/1999 Miller et al. ............... 514/575

FOREIGN PATENT DOCUMENTS

| GB | 1028921 | 5/1966 |
| JP | 3-53891 | 3/1991 |
| JP | 3-157372 | 7/1991 |
| WO | 92/22523 | 12/1992 |
| WO | 94/10990 | 5/1994 |
| WO | 95/06031 | 3/1995 |
| WO | 96/33165 | 10/1996 |
| WO | 98/24474 | 6/1998 |

OTHER PUBLICATIONS

"Matlystatins, New Inhibitors of Type IV Collagenases From *Actinomadura atramentaria* II Biological Activities", Kazuhiko Tanzawa, et al. (1992) The Journal of Antibiotics, vol. 45, No. 11, pp. 1733–1737.

"Inhibition of proteases in *Pseudomonas otitis* media in chinchillas", Cheryl S. Cotter, et al., Otolaryngology—Head and Neck Surgery, (1996), vol. 115, No. 4, pp. 342–351.

"Antibiotic Actinonin I to VIII", J. Chem. Soc. Perkin Trans 1, vol. 9, 1975, pp. 819–860.

"Galardin™ Antiinflammatory protease inhibitor", Richard E. Galardy, Drugs of the Future 1993, 18(12): 109–111.

* cited by examiner

Primary Examiner—Kevin E. Weddington
(74) Attorney, Agent, or Firm—Banner & Witcoff, Ltd.

(57) ABSTRACT

Compounds of formula (I) are antibacterials wherein: $R_1$ represents hydrogen, or $C_1$–$C_6$ alkyl or $C_1$–$C_6$ alkyl substituted by one or more halogen atoms; $R_2$ represents a group $R_{10}$—$(X)_n$—$(ALK)_m$— wherein $R_{10}$ represents hydrogen, or a $C_1$–$C_6$ alkyl, $C_2$–$C_6$ alkenyl, $C_2$–$C_6$ alkynyl, cycloalkyl, aryl, or heterocyclyl group, any of which may be unsubstituted or substituted by $(C_1$–$C_6)$alkyl, $(C_1$–$C_6)$alkoxy, hydroxy, mercapto, $(C_1$–$C_6)$alkylthio, amino, halo (including fluoro, chloro, bromo and iodo), trifluoromethyl, cyano, nitro, —COOH, —$CONH_2$, —$COOR^A$, —$NHCOR^A$, —$CONHR^A$, —$NHR^A$, —$NR^AR^B$, or —$CONR^AR^B$ wherein $R^A$ and $R^B$ are independently a $(C_1$–$C_6)$alkyl group, and ALK represents a straight or branched divalent $C_1$–$C_6$ alkylene, $C_2$–$C_6$ alkenylene, or $C_2$–$C_6$ alkynylene radical, and may be interrupted by one or more non-adjacent —NH—, —O— or —S— linkages, X represents —NH—, —O— or —S—, and m and n are independently 0 or 1; and A represents a group as defined in the specification.

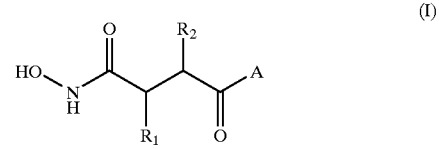

(I)

16 Claims, No Drawings

HYDROXAMIC ACID DERIVATIVES AS ANTIBACTERIALS

This invention relates to the use of hydroxamic acid derivatives as antibacterial agents.

BACKGROUND TO THE INVENTION

In general, bacterial pathogens are classified as either Gram-positive or Gram-negative. Many antibacterial agents (including antibiotics) are specific against one or other Gram-class of pathogens. Antibacterial agents effective against both Gram-positive and Gram-negative pathogens are therefore generally regarded as having broad spectrum activity.

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those which have mechanisms of action fundamentally different from the known classes.

Amongst the Gram-positive pathogens, such as Staphylococci, Streptococci, Mycobacteria and Enterococci, resistant strains have evolved/arisen which makes them particularly difficult to eradicate. Examples of such strains are methicillin resistant *Staphylococcus aureus* (MRSA), methicillin resistant coagulase negative Staphylococci (MRCNS), penicillin resistant *Streptococcus pneumoniae* and multiply resistant *Enterococcus faecium*.

Pathogenic bacteria are often resistant to the aminoglycoside, β-lactam (penicillins and cephalosporins), and chloramphenicol types of antibiotic. This resistance involves the enzymatic inactivation of the antibiotic by hydrolysis or by formation of inactive derivatives. The β-lactam (penicillin and cephalosporin) family of antibiotics are characterised by the presence of a β-lactam ring structure. Resistance to this family of antibiotics in clinical isolates is most commonly due to the production of a "penicillinase" (β-lactamase) enzyme by the resistant bacterium which hydrolyses the β-lactam ring thus eliminating its antibacterial activity.

Recently there has been an emergence of vancomycin-resistant strains of enterococci (Woodford N. 1998 Glycopeptide-resistant enterococci: a decade of experience. Journal of Medical Microbiology. 47(10):849–62). Vancomycin-resistant enterococci are particularly hazardous in that they are frequent causes of hospital based infections and are inherently resistant to most antibiotics. Vancomycin works by binding to the terminal D-Ala-D-Ala residues of the cell wall peptidioglycan precursor. The high-level resistance to vancomycin is known as VanA and is conferred by a genes located on a transposable element which alter the terminal residues to D-Ala-D-lac thus reducing the affinity for vancomycin.

In view of the rapid emergence of multidrug-resistant bacteria, the development of antibacterial agents with novel modes of action that are effective against the growing number of resistant bacteria, particularly the vancomycin resistant enterococci and β-lactam antibiotic-resistant bacteria, such as methicillin-resistant *Staphylococcus aureus,* is of utmost importance.

BRIEF DESCRIPTION OF THE INVENTION

This invention is based on the finding that certain hydroxamic acid derivatives have antibacterial activity, and makes available a new class of antibacterial agents. The inventors have found that the compounds with which this invention is concerned are antibacterial with respect to a range of Gram-positive and Gram-negative organisms.

Although it may be of interest to establish the mechanism of action of the compounds with which the invention is concerned, it is their ability to inhibit bacterial growth which makes them useful. However, it is presently believed that their antibacterial activity is due, at least in part, to intracellular inhibition of bacterial polypeptide deformylase (PDF) enzyme.

Bacterial polypeptide deformylases (PDF) (EC 3.5.1.31), are a conserved family of metalloenzymes (Reviewed: Meinnel T, Lazennec C, Villoing S, Blanquet S, 1997, Journal of Molecular Biology 267, 749–761) which are essential for bacterial viability, their function being to remove the formyl group from the N-terminal methionine residue of ribosome-synthesised proteins in eubacteria. Mazel et al. (EMBO J. 13(4):914–923, 1994) have recently cloned and characterised an *E. coli* PDF. As PDF is essential to the growth of bacteria and there is no eukaryotic counterpart to PDF, Mazel et al. (ibid), Rajagopalan et al. (J. Am. Chem. Soc. 119:12418–12419, 1997) and Becker et al., (J. Biol Chem. 273(19):11413–11416, 1998) have each proposed that PDF is an excellent anti-bacterial target.

The natural antibiotic actinonin (see for example J.C.S Perkin I, 1975, 819) is a hydroxamic acid derivative of Structure (A):

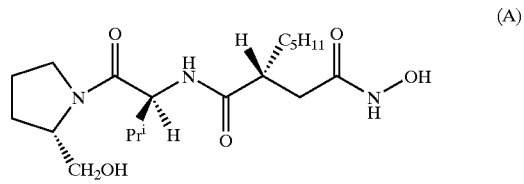

(A)

In addition, various structural analogues of actinonin have also been shown to have antibacterial activity (see for example Broughton et al. (Devlin et al. Journal of the Chemical Society. Perkin Transactions 1 (9):830–841, 1975; Broughton et al. Journal of the Chemical Society. Perkin Transactions 1 (9):857–860, 1975).

Hydroxamic acid derivatives are also known in the field of matrix metalloproteinase (MMP) inhibition. Many examples of the class have been synthesised and their MMP inhibitory properties reported. A smaller number have been reported to be active in animal models of diseases mediated by MMPs, for example various cancers and rheumatoid arthritis. For reviews of the patent literature on hydroxamate MMP inhibitors, see for example Beckett, Exp. Opin. Ther. Patents (1996) 6, 1305–1315, and Beckett & Whittaker, Exp. Opin. Ther. Patents (1998), 8(3), 259–282, and the documents cited therein.

DESCRIPTION OF THE INVENTION

According to the present invention there is provided the use of a compound of formula (I) or a pharmaceutically or veterinarily acceptable salt thereof in the preparation of an antibacterial composition:

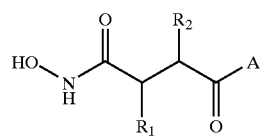

wherein:
R₁ represents hydrogen, or $C_1$–$C_6$ alkyl, $C_1$–$C_6$ alkyl substituted by one or more halogen atoms, amino, hydroxy, or $C_1$–$C_6$ alkoxy;

R₂ represents a group $R_{10}$—$(X)_n$—$(ALK)_m$— wherein
R₁₀ represents hydrogen, or a $C_1$–$C_6$ alkyl, $C_2$–$C_6$ alkenyl, $C_2$–$C_6$ alkynyl, cycloalkyl, aryl, or heterocyclyl group, any of which may be unsubstituted or substituted by ($C_1$–$C_6$)alkyl, ($C_1$–$C_6$)alkoxy, hydroxy, mercapto, ($C_1$–$C_6$)alkylthio, amino, halo (including fluoro, chloro, bromo and iodo), trifluoromethyl, cyano, nitro, —COOH, —CONH₂, —COOR$^A$, —NHCOR$^A$, —CONHR$^A$, —NHR$^A$, —NR$^A$R$^B$, or —CONR$^A$R$^B$ wherein R$^A$ and R$^B$ are independently a ($C_1$–$C_6$)alkyl group, and ALK represents a straight or branched divalent $C_1$–$C_6$ alkylene, $C_2$–$C_6$ alkenylene, or $C_2$–$C_6$ alkynylene radical, and may be interrupted by one or more non-adjacent —NH—, —O— or —S—linkages,
X represents —NH—, —O— or —S—, and
m and n are independently 0 or 1; and
A represents (i) a group of formula (IA), (IB), (IC) or (ID)

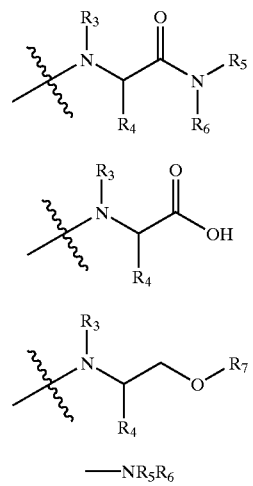

wherein:
R₃ represents hydrogen or $C_1$–$C_6$ alkyl and R₄ represents the side chain of a natural or non-natural alpha amino acid or R₃ and R₄ when taken together with the nitrogen and carbon atoms to which they are respectively attached form an optionally substituted saturated heterocyclic ring of 5 to 8 atoms which ring is optionally fused to a carbocyclic or second heterocyclic ring, R₅ and R₆, independently represent hydrogen, or optionally substituted $C_1$–$C_8$. alkyl, cycloalkyl, aryl, aryl($C_1$–$C_6$ alkyl), heterocyclic, or heterocyclic ($C_1$–$C_6$ alkyl), or R₅ and R₆ when taken together with the nitrogen atom to which they are attached form an optionally substituted saturated heterocyclic ring of 3 to 8 atoms which ring is optionally fused to a carbocyclic or second heterocyclic ring, and R₇ represents hydrogen, $C_1$–$C_6$ alkyl, or an acyl group.
PROVIDED THAT (a) R₅ and R₆ taken together with the nitrogen atom to which they are attached do not form an optionally substituted saturated heterocyclic ring of 3 to 8 atoms when R₁ and R₃ are hydrogen, R₂ is hydrogen, $C_1$–$C_6$ alkyl, phenyl, benzyl, 4-chlorophenylmethyl, 4-nitrophenylmethyl, or 4-aminophenylmethyl and R₃ is hydrogen, methyl, isopropyl, isobutyl or benzyl; and (b) R₅ is not 2-pyridyl or 2-thiazolyl when R₁, R₃ and R₆ are hydrogen, R₂ is n-pentyl and R₄ is isopropyl; and (c) R₅ and R₆ are not both ethyl when R₁ and R₃ are hydrogen, R₂ is n-pentyl and R₄ is methyl or isopropyl.

In another aspect, the invention provides a method for the treatment of bacterial infections in humans and non-human mammals, which comprises administering to a subject suffering such infection an antibacterially effective dose of a compound of formula (I) as defined above.

In a further aspect of the invention there is provided a method for the treatment of bacterial contamination by applying an antibacterially effective amount of a compound of formula (I) as defined above to the site of contamination.

The compounds of formula (I) as defined above may be used as component(s) of antibacterial cleaning or disinfecting materials.

According to a preferred embodiment, the various aspects of the invention can be applied against vancomycin-, quinolone- and "β-lactam"-resistant bacteria and the infections they cause.

On the hypothesis that the compounds (I) act by inhibition of intracellular PDF, the most potent antibacterial effect may be achieved by using compounds which efficiently pass through the bacterial cell wall. Thus, compounds which are highly active as inhibitors of PDF in vitro and which penetrate bacterial cells are preferred for use in accordance with the invention. It is to be expected that the antibacterial potency of compounds which are potent inhibitors of the PDF enzyme in vitro, but are poorly cell penetrant, may be improved by their use in the form of a prodrug, ie a structurally modified analogue which is converted to the parent molecule of formula (I), for example by enzymic action, after it has passed through the bacterial cell wall.

As used herein the term "($C_1$–$C_6$)alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

As used herein the term "divalent ($C_1$–$C_6$)alkylene radical" means a saturated hydrocarbon chain having from 1 to 6 carbon atoms and two unsatisfied valencies.

As used herein the term "($C_2$–$C_6$)alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl.

As used herein the term "divalent ($C_2$–C6)alkenylene radical" means a hydrocarbon chain having from 2 to 6 carbon atoms, at least one double bond, and two unsatisfied valencies.

As used herein the term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent $(C_2–C_6)$alkynylene radical" means a hydrocarbon chain having from 2 to 6 carbon atoms, at least one triple bond, and two unsatisfied valencies.

As used herein the term "cycloalkyl" means a saturated alicyclic moiety having from 3–8 carbon atoms and includes, for example, cyclopropyl, cyclobutyl, cyclopentyl, cyclohexyl, cycloheptyl and cyclooctyl.

As used herein the term "cycloalkenyl" means an unsaturated alicyclic moiety having from 3–8 carbon atoms and includes, for example, cyclopropenyl, cyclobutenyl, cyclopentenyl, cyclohexenyl, cycloheptenyl and cyclooctenyl. In the case of cycloalkenyl rings of from 5–8 carbon atoms, the ring may contain more than one double bond.

As used herein the term "aryl" refers to a mono-, bi- or tri-cyclic carbocyclic aromatic group, and to groups consisting of two covalently linked monocyclic carbocyclic aromatic groups. Illustrative of such groups are phenyl, biphenyl and napthyl.

As used herein the term "heteroaryl" refers to a 5- or 6-membered aromatic ring containing one or more heteroatoms, and optionally fused to a benzyl or pyridyl ring; and to groups consisting of two covalently linked 5- or 6- membered aromatic rings each containing one or more heteroatoms; and to groups consisting of a monocyclic carbocyclic aromatic group covalently linked to a 5- or 6-membered aromatic rings containing one or more heteroatoms;. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, 4-([1,2,3]-thiadiazoly-4-yl)phenyl and 5-isoxazol-3-ylthienyl.

As used herein the unqualified term "heterocyclyl" or "heterocyclic" includes "heteroaryl" as defined above, and in particular means a 5–7 membered aromatic or non-aromatic heterocyclic ring containing one or more heteroatoms selected from S, N and O, and optionally fused to a benzene ring, including for example, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido and 1,3-dioxo-1,3-dihydro-isoindol-2-yl groups.

As used herein the term "acyl" means a group $R_{20}C(O)$— where $R_{20}$ is $(C_1–C_6)$alkyl, $(C_2–C_6)$alkenyl, $(C_3–C_7)$cycloalkyl, phenyl, heterocyclyl, phenyl$(C_1–C_6)$alkyl, heterocyclyl$(C_1–C_6)$alkyl, $(C_3–C_7)$cycloalkyl$(C_1–C_6)$alkyl, phenyl$(C_2–C_6)$alkenyl, heterocyclyl$(C_2–C_6)$alkenyl, $(C_3–C_7)$cycloalkyl$(C_2–C_6)$alkenyl, any of which $R_{20}$ groups may be substituted.

Unless otherwise specified in the context in which it occurs, the term "substituted" as applied to any moiety herein means substituted with up to four substituents, each of which independently may be $(C_1–C_6)$alkyl, benzyl, $(C_1–C_6)$alkoxy, phenoxy, hydroxy, mercapto, $(C_1–C_6)$alkylthio, amino, halo (including fluoro, chloro, bromo and iodo), trifluoromethyl, nitro, —COOH, —CONH$_2$, —COR$^A$, —COOR$^A$, —NHCOR$^A$, —CONHR$^A$, —NHR$^A$, —NR$^A$R$^B$, or—CONR$^A$R$^B$ wherein R$^A$ and R$^B$ are independently a $(C_1–C_6)$alkyl group. In the case where "substituted" means benzyl, the phenyl ring thereof may itself be substituted with any of the foregoing, except benzyl.

As used herein the terms "side chain of a natural alpha-amino acid" and "side chain of a non-natural alpha-amino acid" mean the group R$^x$ in respectively a natural and non-natural amino acid of formula NH$_2$—CH(R$^x$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

In natural alpha-amino acid side chains which contain functional substituents, for example amino, carboxyl, hydroxy, mercapto, guanidyl, imidazolyl, or indolyl groups as in arginine, lysine, glutamic acid, aspartic acid, tryptophan, histidine, serine, threonine, tyrosine, and cysteine, such functional substituents may optionally be protected.

Likewise, in the side chains of non-natural alpha amino acids which contain functional substituents, for example amino, carboxyl, hydroxy, mercapto, guanidyl, imidazolyl, or indolyl groups, such functional substituents may optionally be protected.

The term "protected" when used in relation to a functional substituent in a side chain of a natural or non-natural alpha-amino acid means a derivative of such a substituent which is substantially non-functional. The widely used handbook by T. W. Greene and P. G. Wuts "Protective Groups in Organic Synthesis" Second Edition, Wiley, New York, 1991 reviews the subject. For example, carboxyl groups may be esterified (for example as a $C_1–C_6$ alkyl ester), amino groups may be converted to amides (for example as a NHCOC$_1$–C$_6$ alkyl amide) or carbamates (for example as an NHC(=O)OC$_1$–C$_6$ alkyl or NHC(=O)OCH$_2$Ph carbamate), hydroxyl groups may be converted to ethers (for example an OC$_1$–C$_6$ alkyl or a O(C$_1$–C$_6$ alkyl)phenyl ether) or esters (for example a OC(=O)C$_1$–C$_6$ alkyl ester) and thiol groups may be converted to thioethers (for example a tert-butyl or benzyl thioether) or thioesters (for example a SC(=O)C$_1$–C$_6$ alkyl thioester).

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several actual or potential chiral centres in the compounds according to the invention because of the presence of asymmetric carbon atoms. The presence of several asymmetric carbon atoms gives rise to a number of diastereoisomers with R or S stereochemistry at each chiral centre. The invention includes all such diastereoisomers and mixtures thereof. Currently, the preferred stereoconfiguration of the carbon atom carrying the $R_2$ group is R; that of the carbon atom carrying the $R_4$ group (when asymmetric) is S; and that of the carbon atom carrying the $R_1$ group (when asymmetric) is R.

In the compounds for use according to the invention and in the novel compounds of the invention:

$R_1$ may be, for example, hydrogen, hydroxy, methoxy, methyl, or trifuoromethyl. Hydrogen is currently preferred.

$R_2$ may be, for example:
optionally substituted $C_1–C_8$ alkyl, $C_3–C_6$ alkenyl, $C_3–C_6$ alkynyl or cycloalkyl;
phenyl$(C_1–C_6$ alkyl)-, phenyl$(C_3–C_6$ alkenyl)- or phenyl$(C_3–C_6$ alkynyl)- optionally substituted in the phenyl ring;
cycloalkyl$(C_1–C_6$ alkyl)-, cycloalkyl$(C_3–C_6$ alkenyl)- or cycloalkyl$(C_3–C_6$ alkynyl)- optionally substituted in the cycloalkyl ring;

heterocyclyl($C_1$–$C_6$ alkyl)-, heterocyclyl($C_3$–$C_6$ alkenyl)- or heterocyclyl($C_3$–$C_6$ alkynyl)- optionally substituted in the heterocyclyl ring; or
$CH_3(CH_2)_pO(CH_2)_q$— or $CH_3(CH_2)_pS(CH_2)_q$—, wherein p is 0, 1, 2 or 3 and q is 1, 2 or 3.

Specific examples of $R_2$ groups include
methyl, ethyl, n- and iso-propyl, n- and iso-butyl, n-pentyl, iso-pentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, and 4-methoxybenzyl.

Presently preferred groups at $R_2$ are n-propyl, n-butyl, n-pentyl, benzyl and cyclopentylmethyl.

$R_3$ may be, for example, hydrogen or methyl, with hydrogen presently preferred.

$R_4$ may be, for example
the characterising group of a natural α-amino acid, for example isopropyl, benzyl, or 4-hydroxyphenylmethyl, in which any functional group may be protected, any amino group may be acylated and any carboxyl group present may be amidated; or a group —[Alk]$_n$R$_9$ where Alk is a ($C_1$–$C_6$)alkylene or ($C_2$–$C_6$)alkenylene group optionally interrupted by one or more —O—, or —S—atoms or —N($R_2$)— groups [where $R_{12}$ is a hydrogen atom or a ($C_1$–$C_6$) alkyl group], n is 0 or 1, and $R_9$ is hydrogen or an optionally substituted phenyl, aryl, heterocyclyl, cycloalkyl or cycloalkenyl group or (only when n is 1) $R_9$ may additionally be hydroxy, mercapto, ($C_1$–$C_6$)alkylthio, amino, halo, trifluoromethyl, nitro, —COOH, —CONH$_2$, —COOR$^A$, —NHCOR$_A$, —CONHR$^A$, —NHR$^A$, —NR$^A$R$^B$, —CONR$^A$R$^B$ wherein R$^A$ and R$^B$ are independently a ($C_1$–$C_6$)alkyl group; or a benzyl group substituted in the phenyl ring by a group of formula —OCH$_2$COR$_8$ where $R_8$ is hydroxyl, amino, ($C_1$–$C_6$)alkoxy, phenyl($C_1$–$C_6$)alkoxy, ($C_1$–$C_6$)alkylamino, di(($C_1$–$C_6$)alkyl)amino, phenyl ($C_1$–$C_6$)alkylamino; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–C6)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or a group —CR$_a$R$_b$R$_c$ in which:
each of $R_a$, $R_b$ and $R_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl; or
$R_c$ is hydrogen and $R_a$ and $R_b$ are independently phenyl or heteroaryl such as pyridyl; or
$R_c$ is hydrogen, ($C_1$–$C_6$)alkyl, ($C_2$–$C_6$)alkenyl, ($C_2$–$C_6$)alkynyl, phenyl($C_1$–$C_6$)alkyl, or ($C_3$–$C_8$) cycloalkyl, and $R_a$ and $R_b$ together with the carbon atom to which they are attached form a 3- to 8- membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$)alkenyl, ($C_2$–$C_6$)alkynyl, phenyl($C_1$–$C_6$) alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_1$–$C_4$)perfluoroalkyl, —CH$_2$OH, —CO$_2$($C_1$–$C_6$)alkyl, —O($C_1$–$C_6$)alkyl, —O($C_2$–$C_6$)alkenyl, —S($C_1$–$C_6$)alkyl, —SO ($C_1$–$C_6$)alkyl, —SO$_2$($C_1$–$C_6$)alkyl, —S($C_2$–$C_6$) alkenyl, —SO($C_2$–$C_6$)alkenyl, —SO$_2$($C_2$–$C_6$) alkenyl or a group —Q—W wherein Q represents a bond or —O—, —S—, —SO—or —SO$_2$— and W represents a phenyl, phenylalkyl, ($C_3$–$C_8$) cycloalkyl, ($C_3$–$C_8$)cycloalkylalkyl, ($C_4$–$C_8$) cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$ ($C_1$–$C_6$)alkyl, —CONH$_2$, —CONH($C_1$–$C_6$)alkyl, —CONH($C_1$–$C_6$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$ ($C_1$–$C_6$)alkyl, —NO$_2$, —NH$_2$, —NH($C_1$–$C_6$) alkyl, —N(($C_1$–$C_6$)alkyl)$_2$, —NHCO($C_1$–$C_6$) alkyl, ($C_1$–$C_6$)alkyl, ($C_2$–$C_6$)alkenyl, ($C_2$–$C_6$) alkynyl, ($C_3$–$C_8$)cycloalkyl, ($C_4$–$C_8$)cycloalkenyl, phenyl or benzyl.

Examples of particular $R_4$ groups include methyl, ethyl, isopropyl, benzyl, 4-chlorobenzyl, 4-hydroxybenzyl, phenyl, cyclohexyl, cyclohexylmethyl, pyridin-3-ylmethyl, tert-butoxymethyl, naphthylmethyl, iso-butyl, sec-butyl, tert-butyl, 1-benzylthio-1-methylethyl, 1-methylthio-1-methylethyl, 1-mercapto-1-methylethyl, 1-methoxy-1-methylethyl, 1-hydroxy-1-methylethyl, 1-fluoro-1-methylethyl, 4,4-dimethyl-prop-1-en-4-yl, 4,4-dimethyl-prop4-yl hydroxymethyl, 2-hydroxyethyl, 2-carboxyethyl, 2-methylcarbamoylethyl, 2-carbamoylethyl, and 4-aminobutyl. Presently preferred $R_4$ groups include tert-butyl, iso-butyl, benzyl and methyl.

$R_3$ and $R_4$ when taken together with the nitrogen and carbon atoms to which they are respectively attached may form an optionally substituted saturated heterocyclic ring of 5 to 8 atoms. For example, $R_3$ and $R_4$ may form a bridge between the nitrogen and carbon atoms to which they are attached, said bridge being represented by the divalent radical —(CH$_2$)$_{3-6}$—, or —(CH$_2$)$_r$—O—(CH$_2$)$_s$—, or —(CH$_2$)$_r$ —S—(CH$_2$) $_s$—, wherein r and s are each independently 1, 2 or 3 with the proviso that r+s=2, 3, 4, or 5.

$R_5$ and $R_6$ may independently be, for example, hydrogen, methyl, ethyl, tert-butyl, n-heptyl, cyclopentyl, cyclohexyl, phenyl,2-ethoxycarbonyl-eth-2-yl, pyrid-2-yl, 1,1,3,3-tetramethylbutyl, benzyl, 2,6-dimethyl-4-tert-butyl-phenyl,diphenylmethyl, 4-chlorophenyl-phenylmethyl, 2-fluorophenyl-phenylmethyl, 1-(4- fluorophenyl)-1-phenyl-1-amino-methyl, 1,1-diphenylprop-3-yl, 3-phenyl-thiazolyl, or 2-hydroxyethyl;

or $R_5$ and $R_6$ when taken together with the nitrogen atom to which they are attached may form a saturated 5- to 8-membered monocyclic N-heterocyclic ring which is attached via the N atom and which optionally contains —N($R_{11}$)—wherein $R_{11}$ is hydrogen or $C_1$–$C_6$ alkyl, benzyl, acyl, or an amino protecting group, O, S, SO or $SO_2$ as a ring member, and/or is optionally substituted on one or more C atoms by hydroxy, $C_1$–$C_6$ alkyl, hydroxy($C_1$–$C_6$ alkyl)-, $C_1$–$C_6$ alkoxy, oxo, ketalised oxo, amino, mono($C_1$–$C_6$ alkyl)amino, di($C_1$–$C_6$ alkyl) amino, carboxy, $C_1$–$C_6$ alkoxycarbonyl, hydroxymethyl, $C_1$–$C_6$ alkoxymethyl, carbamoyl, mono($C_1$–$C_6$ alkyl)carbamoyl, di($C_1$–$C_6$ alkyl) carbamoyl, or hydroxyimino.

Examples of such rings are substituted or unsubstituted 1-pyrrolidinyl, piperidin-1-yl, 1-piperazinyl, hexahydro-1-pyridazinyl, morpholin-4-yl, tetrahydro-1,4-thiazin-4-yl, tetrahydro-1,4-thiazin-4-yl 1-oxide, tetrahydro-1,4-thiazin-4-yl 1,1-dioxide, hexahydroazipino, or octahydroazocino. Substituted examples of the foregoing are 2-(methylcarbamoyl)-1-pyrrolidinyl, 2-(hydroxymethyl)-1-pyrrolidinyl, 4-hydroxypiperidino, 2-(methylcarbamoyl) piperidino, 4-hydroxyiminopiperidino, 4-methoxypiperidino, 4-methylpiperidin-1yl, 4-benzylpiperidin-1-yl, 4-acetylpiperidin-1-yl,4-methyl-1-piperazinyl, 4-phenyl-1-piperazinyl, 1,4-dioxa-8-azaspiro[4,5]decan-8-yl, hexahydro-3-(methylcarbamoyl)-2-pyridazinyl, and hexahydro-1-(benzyloxycarbonyl)-2-pyridazinyl, decahydroisoquinolin-2-yl, and 1,2,3,4-tetrahydroisoquinolin-2-yl.

When A is a group of formula (IA), it is currently preferred that $R_5$ be methyl or hydrogen, and $R_6$ be methyl.

$R_7$ may be, for example, hydrogen, or a group $R_{20}C(O)$— where $R_{20}$ is a ($C_1$–$C_6$)alkyl group such as methyl or ethyl.

A specific example of a compound having PDF inhibiting and antibacterial activity in accordance with the invention is:
$N^1$—(1S-dimethylcarbamoyl-2,2-dimethyl-1-propyl)-$N^4$-hydroxy-2R-butyl-succinamide
and pharmaceutically acceptable salts, hydrates and solvates thereof.

Compounds for use in accordance with the invention may be prepared by methods described in the literature for the preparation of hydroxamate MMP inhibitors, for example the patent publications relating to such compounds cited in Beckeft, Exp. Opin. Ther. Patents (1996) 6, 1305–1315, and Beckett & Whittaker, Exp. Opin. Ther. Patents (1998), 8(3), 259–282.

Compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tableting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the active ingredient(s) may be made up into a cream, lotion or ointment. Cream or ointment formulations which may be used for the drug are conventional formulations well known in the art, for example as described in standard textbooks of pharmaceutics such as the British Pharmacopoeia.

The active ingredient(s) may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples are of compounds of formula (I) above having PDF inhibiting activity and antibacterial activity in accordance with the invention $^1$H and $^{13}$C NMR spectra were recorded using a Bruker AC 250E spectrometer at 250.1 and 62.9 MHz, respectively. Elemental microanalyses were performed by MEDAC Ltd. Department of Chemistry, Brunel University, Uxbridge, Middlesex UB8 3PH. L-Tert-leucine-N-methylamide was prepared according to established literature methods.

EXAMPLE 1

$N^1$-(1S-Methylcarbamoyl-2-phenyl-ethyl)-$N^4$-hydroxy-2R-propyl-succinamide

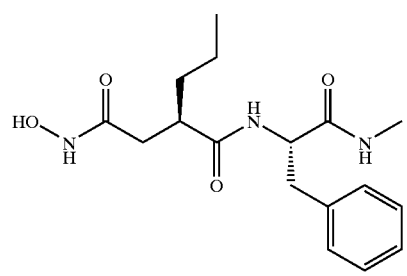

The title compound was prepared by the method described in WO 92/13831 (Example 1), substituting valeryl chloride for 4-methylvaleryl chloride.

m.p.=191–193° C. $^1$H-NMR δ (CD$_3$OD, partial D exchange); 8.12 (0.5H, d, J=8.1Hz), 7.96–7.87 (5H, m), 4.55–4.40 (1H, m), 3.11 (1H, dd, J=6.4, 13.7Hz), 2.89 (1H, dd, J=8.9, 13.7Hz), 2.65, 2.63 (3H, 2s), 2.60–2.50 (1H, m), 2.20 (1H, dd, J=8.0, 14.6Hz), 2.06 (1H, dd, J=6.7, 14.6Hz), 1.48–1.00 (4H, m) and 0.78 (3H, t, J=7.1Hz). $^{13}$C-NMR δ (CD$_3$OD); 177.0, 174.0, 170.8, 138.8, 130.3, 129.4, 127.7, 56.3, 44.4, 38.7, 36.4, 35.6, 26.3 21.3 and 14.3. IR (KBr, ν$_{max}$ cm$^{-1}$); 3292, 2957, 1637, 1560 and 1541. Found: C 60.18, H 7.45, N 12.52%; C$_{17}$H$_{25}$N$_3$O$_4$0.2H$_2$0 requires C 60.23, H 7.55, N 12.39%.

The compounds of Examples 2 and 3 were prepared by analogy with Example 1.

EXAMPLE 2

N$^1$-(1S-Methylcarbamoyl-2,2-dimethyl-propyl)-N$^4$-hydroxy-2R-propyl-succinamide

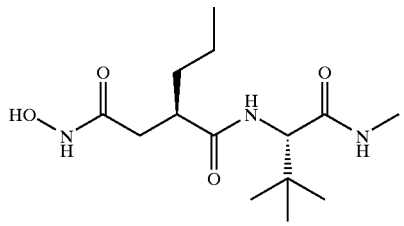

m.p. 200° C. $^1$H-NMR (CD$_3$OD); 4.19 (1H, s), 2.90–2.76 (1H, m), 2.68 (3H, s),2.31 (1H, dd, J=7.9, 14.6 Hz), 2.15 (1H, dd, J=6.5, 14.6 Hz), 1.60–1.40 (1H, m), 1.40–1.14 (3H, m), 0.95 (9H, s) and 0.85 (3H, t, J=7.0 Hz). $^{13}$C-NMR (CD$_3$OD); 176.9, 173.3, 170.7, 62.2, 43.6, 36.5, 35.7, 35.3, 27.17, 26.0, 21.4 and 14.4. IR (KBr, ν$_{max}$ cm$^{-1}$); 1682, 1634, 1544, 1470, 1413, 1369 and 1248. Found C 55.35 H 8.84 N 13.92%; C$_{14}$H$_{27}$N$_3$O$_4$ requires C 55.79, H 9.03, N 13.94%.

EXAMPLE 3

N$^1$-(1S-Dimethylcarbamoyl-2,2-dimethyl-1-propyl)-N$^4$-hydroxy-2R-butyl-succinamide

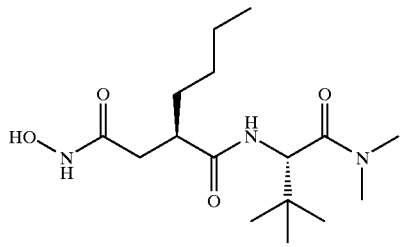

Off white solid. m.p. 165–166° C. $^1$H-NMR; δ (CDCl$_3$), 4.87 ($_1$H, s), 3.19 (3H, s), 2.93 (3H, s), 2.83 (1H, m), 2.35 (1H, dd, J=7.8, 14.6 Hz), 2.19 (1H, dd, J=6.3, 14.5 Hz), 1.59–1.06 (6H, br m), 1.01 (9H, s) and 0.87 (3H, t, J=6.9 Hz). $^1$H-NMR; δ (CDCl$_3$), 177.5, 173.6, 171.1, 71.1, 56.6, 42.3, 39.2, 36.6, 36.4, 33.6, 30.8, 27.5, 24.0 and 14.7. LRMS: +ve ion 352 [M+Na], −ve ion 328 [M−H].

EXAMPLE 4

By methods described in the literature analogous to those used for Example 1–3 above, the following compounds of formula (I) above, wherein A is a group of formula (IA) were prepared:

| $R_1$ | $R_2$ | $R_3$ | $R_4$ | $R_5$ | $R_6$ |
|---|---|---|---|---|---|
| H | cyclopentyl-methyl | H | benzyl | H | methyl |
| H | iso-butyl | H | iso-propyl | H | methyl |
| H | iso-butyl | H | benzyl | H | phenyl |
| H | iso-butyl | H | tert-butyl | H | phenyl |
| H | iso-butyl | H | 1-methyl-1-methylthioethyl | H | methyl |
| H | HO(CH$_2$)$_{14}$— | H | tert-butyl | H | methyl |
| H | cyclopentyl-methyl | H | tert-butyl | H | tert-butyl |
| H | cyclopentyl-methyl | H | 4,4-dimethyl-prop-1-en-4-yl | H | cyclohexyl |
| H | cyctopentyl-methyl | H | 4,4-dimethyl-prop-4-yl | H | cyclohexyl |
| H | iso-butyl | H | tert-butyl | H | methyl |
| H | iso-butyl | H | iso-butyl | H | 2-ethoxycarbonyl-eth-2-yl |
| H | iso-butyl | H | tert-butyl | H | tert-butyl |
| H | iso-butyl | H | tert-butyl | methyl | methyl |
| H | iso-butyl | H | tert-butyl | H | pyrid-2-yl |
| H | cyclopentyl-methyl | H | tert-butyl | H | benzyl |
| OH | iso-butyl | H | tert-butyl | H | 2,6-dimethyl-4-tert-butyl-phenyl |
| OH | iso-butyl | H | tert-butyl | H | diphenylmethyl |
| OH | iso-butyl | H | tert-butyl | H | 4-chlorophenyl-phenylmethyl |
| OH | iso-butyl | H | tert-butyl | H | 1,1-diphenylprop-3-yl |
| OH | iso-butyl | H | tert-butyl | H | 3-phenyl-thiazolyl |
| OH | iso-butyl | H | tert-butyl | H | 1-(4-fluoro-phenyl)-1-phenyl-1-amino-methyl |
| OH | iso-butyl | H | tert-butyl | H | 2-fluorophenyl-phenylmethyl |

EXAMPLE 5

N$^1$-(1R, S-tert-Butylcarbamoyl-2,2-dimethyl-1-propyl)-N$^4$-hydroxy-2R-butyl-succinamide

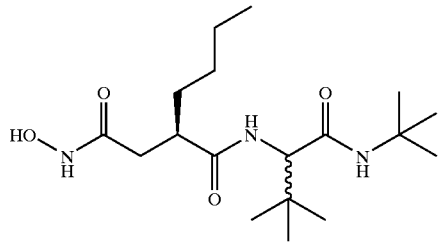

The title compound was prepared by Ugi reaction of the appropriate homochiral succinate ester with trimethylacetaldehyde and ammonia, followed by conversion to the desired hydroxamic acid, as described in GB-2298423-A. The starting succinates were prepared by the method described in WO 92/13831.

$^1$H-NMR: δ (CD$_3$OD; mixture of diastereoisomers); 7.39 (0.5 H, s), 7.32 (0.5 H, s), 4.08 (0.5 H, s) 4.02 (0.5H, 2s), 2.80–2.70 (1H, m), 2.32–2.19 (1H, m), 2.18–2.00 (1 H m), 1.60–1.04 (6H, m), 1.22 (4.5H, s), 1.21 (4.5H, s), 0.90 (4.5H, s), 0.87 (4.5H, s) and 0.85–0.76 (3H, m). $^3$C-NMR (CD$_3$OD); 177.0, 176.8, 171.8, 170.9, 62.8, 62.2, 52.2, 52.1, 43.8, 43.7, 36.6, 36.4, 35.8, 35.4, 35.3, 35.1, 28.9, 28.8, 27.4, 27.2, 21.5, 21.4, 14.3 and 14.3. IR (KBr, ν$_{max}$ cm$^{-1}$); 3313, 2963, 1637, 1546, 1456, 1395, 1364, 1264, 1225 and 1188.

EXAMPLE 6

6-Biphenyl-4-yl-3R-(piperidine-1-carbonyl)-hexanoic acid hydroxyamide

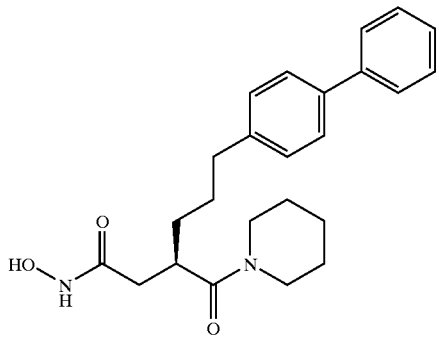

The title compound was prepared by a method analogous to that used for the preparation of compounds of Examples 1–4, except that piperidine was used in the coupling reaction in place of the amino acid derivative.

m.p. 149–150° C. $^1$H-NMR: δ ((CD$_3$)$_2$SO), 10.37 (1H, s), 8.69 (1H, s), 7.69–7.19 (9H, m), 3.59–3.24 (4H, m), 3.24–3.08 (1H, m), 2.65–2.43 (2H, m), 2.25 (1H, dd, J=7.8, 14.6Hz), 2.01 (1H, dd, J=6.0, 14.7 Hz) and 1.64–1.20 (10H, m). $^3$C-NMR; δ ((CD$_3$)$_2$SO), 172.3, 168.0, 141.6, 140.5, 138.0, 129.3, 127.5, 126.9, 126.8, 46.4, 42.6, 36.3, 35.4, 35.1, 31.8, 28.5, 26.5, 25.8 and 24.5. IR (reflection disc, $v_{max}$, cm$^{-1}$); 3230, 2939, 2855, 1659, 1612, 1461.

Biologucal Example A i) Cloning of the *Escherichia coli* PDF Gene.

The *E. coli* PDF gene was cloned in pET24a(+) (designated pET24-PDF) and was used to transform BL21 DE3 cells from Novagen Inc, (Madison, Wis.). Clones were selected at 37° C. on YT agar plates (8g/l typtone, 5g/yeast extract, NaCl 5 g/l, agar 15 g/l) supplemented with 30 μg/ml kanamycin.

ii) Expression of PDF

A 20m overnight culture of BL21 DE3 cells harbouring pET24-PDF was used to infect 500 ml 2×YT broth (16 g/l typtone, 10 g/l yeast extract, NaCl 5 g/l) containing 30 ug/ml kanamycin in a 2 liter baffled flask and grown at 37° C. with shaking to an OD$_{600}$ 0.6. The culture was then induced by adjusting the medium to 1.0 mM isopropyl β-D thiogalactopyranoside (IPTG). The induction was allowed to proceed for a further 3 hours at 37° C., the cells were harvested by centrifugation and the cell pellet washed with 250 ml phosphate buffered saline (PBS) and the pellet stored at −70° C.

iii) Preparation of Soluble Protein Fraction

The cells from a 1 liter expression were resuspeneded in 2×25 ml of ice cold phosphate buffered saline. The cell suspension was sonicated on ice using an MSE Soniprep 150 fitted with a medium probe and at an amplitude of 20–25 microns in 6×20 second pluses. The resulting suspension was then cleared by centrifugation at 20,000×g for 15 minutes. The supernatant was then used for further purification of the enzyme.

iv) PDF Purification

*E. coli* lysate from a 1 l culture in phosphate buffered saline (PBS) were adjusted to 2M ammonium sulphate. A 15 ml phenyl sepharose column was equilibrated with PBS/2M ammonium sulphate at 4° C. The lysate was loaded on the column and washed with equilibration buffer. The column was eluted by reducing the ammonium sulphate concentration from 2M to 0M over 10 column volumes. 5 ml fractions were collected and analysed by SDS-PAGE. The fractions containing the majority of the 20 kDa PDF were pooled. The pooled fractions were concentrated using a 3 kDa cutoff membrane to a volume of 5 ml. The fraction was then loaded onto a Superdex 75 (size exclusion chromatography) column equilibrated in PBS. The concentrated PDF pool eluted at one ml/min at 4° C. and 5 ml fractions collected and analysed by SDS-PAGE. The purest fractions were pooled and stored at −70° C.

(v) PDF in Vitro Assay

The assay was performed in a single 96 well plate in a final volume of 100 μl containing:

20 μl PDF (4 μg/ml)

20 μl 100 mM Hepes pH 7.0+1M KCl+0.05% Brij

10 μl serial dilution of test compound in 20% DMSO

50 μl formyl-Met-Ala-Ser (8 mM)

The assay was incubated at 37° C. for 30 minutes. The free amino group of the deformylated (Met-Ala-Ser) product was detected using fluorescamine, by the following additions:

50 μ0.2M borate pH 9.5

50 μl fluorescamine (150 μg/ml in dry dioxane)

Fluorescence was quantified on SLT Fluostar plate reader using an excitation wavelength of 390 nM and an emission wavelength of 485 nM. Standard control reactions are a no inhibitor reaction which provides the zero inhibition figure and a no enzyme and no inhibitor reaction which provides the 100% inhibition figure. The data was analysed by conversion of the fluorescence units to % inhibition and the inhibitor concentration plotted against % inhibition. The data was fitted to a sigmoidal function: $y=A+((B-A)/(1+((C/x)^P)))$, wherein A represents zero inhibition, B represents 100% inhibition and C represents the IC$_{50}$, D represents the slope. The IC$_{50}$ represents the concentration of inhibitor (nM) required to decrease enzyme activity by 50%.

The test compounds were found to inhibit bacterial PDF in vitro.

Biological Example B

Minimal inhibitory concentrations (MIC) of the test compounds against *E. coli* strain DH5α (Genotype; F-φ80dlacZΔM15Δ(lacZYA-argF)U169 deoR recA1 endA1 hsdR17($r_k^-$, $m_k^+$)phoA supE44 λ$^-$thi-1 gyrA96 relA1) obtained from GibcoBRL Life Technologies, were determined as follows. Stock solutions of test compound were prepared by dissolution of each compound in dimethylsulfoxide at 10 mM. For the determination of the minimal inhibitory concentration, two fold serial dilutions were prepared in 2×YT broth (typtone 16 g/l, yeast extract 10 g/l, sodium chloride 5 g/l obtained from BIO 101 Inc, 1070 Joshua Way, Vista, Calif. 92083, USA) to yield 0.05 ml compound-containing medium per well. Inocula were prepared from cultures grown overnight in 2×YT broth at 37° C. Cell densities were adjusted to absorbance at 660 nm ($A_{660}$)=0.1; the optical density-standardized preparations were diluted 1:1000 in 2×YT broth; and each well inoculated with 0.05 ml of the diluted bacteria. Microtiter plates were incubated at 37° C. for 18 hours in a humidified incubator. The test compounds had MIC's of 200μM or less against one or both of the test organisms.

What is claimed is:

1. A method for the treatment of bacterial infections in humans and non-human mammals, which comprises inhibiting bacterial growth by administering to a subject an antibacterially effective dose of a compound of formula (I) or a pharmaceutically or veterinarily acceptable salt thereof:

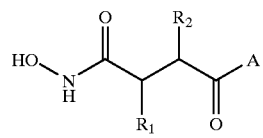

(I)

wherein:

$R_1$ represents hydrogen, or $C_1$–$C_6$ alkyl, $C_1$–$C_6$ alkyl substituted by one or more halogen atoms, amino, hydroxy, or $C_1$–$C_6$ alkoxy;

$R_2$ represents a group $R_{10}$—$(X)_n$—$(ALK)_m$— wherein $R_{10}$ represents hydrogen, or a $C_1$–$C_6$ alkyl, $C_2$–$C_6$ alkenyl, $C_2$–$C_6$ alkynyl, cycloalkyl, aryl, or heterocyclyl group, any of which may be unsubstituted or substituted by $C_1$–$C_6$ alkyl, $C_1$–$C_6$ alkoxy, hydroxy, mercapto, $C_1$–$C_6$ alkylthio, amino, halo, trifluoromethyl, cyano, nitro, —COOH, —CONH$_2$, —COOR$^A$, —NHCOR$^A$, —CONHR$^A$, —NHR$^A$, —NR$^A$R$^B$, or —CONR$^A$R$^B$ wherein R$^A$ and R$^B$ are independently a ($C_1$–$C_6$) alkyl group, and ALK represents a straight or branched divalent $C_1$–$C_6$ alkylene, $C_2$–$C_6$ alkenylene, or $C_2$–$C_6$ alkynylene radical, and may be interrupted by one or more non-adjacent —NH—, —O— or —S— linkages, X represents —NH—, —O—, or —S—, and m and n are independently 0 or 1; and A represents (i) a group of formula (IA), (IB), (IC), or (ID)

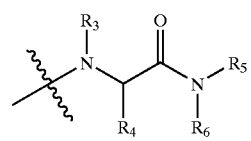

(IA)

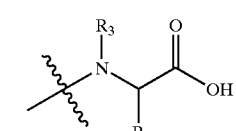

(IB)

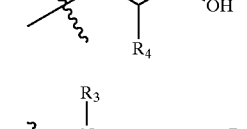

(IC)

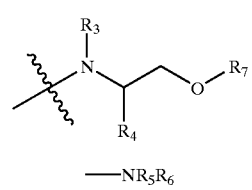

(ID)

—NR$_5$R$_6$ wherein:

$R_3$ represents hydrogen or $C_1$–$C_6$ alkyl and $R_4$ represents the side chain of a natural or non-natural alpha amino acid or $R_3$ and $R_4$ when taken together with the nitrogen and carbon atoms to which they are respectively attached form an optionally substituted saturated heterocyclic ring of 5 to 8 atoms which ring is optionally fused to a carbocyclic or second heterocyclic ring, PROVIDED THAT the fragment of fragment

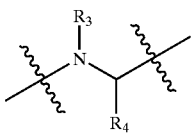

in (IA) is not a fragment of formula

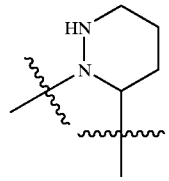

$R_5$ and $R_6$, independently represent hydrogen, or optionally substituted $C_1$–$C_8$ alkyl, cycloalkyl, aryl, aryl ($C_1$–$C_6$ alkyl), heterocyclic, or heterocyclic ($C_1$–$C_6$ alkyl), or $R_5$ and $R_6$ when taken together with the nitrogen atom to which they are attached form an optionally substituted saturated heterocyclic ring of 3 to 8 atoms which ring is optionally fused to a carbocyclic or second heterocyclic ring, and $R_7$ represents hydrogen, $C_1$–$C_6$ alkyl, or an acyl group.

PROVIDED THAT (a) $R_5$ and $R_6$ taken together with the nitrogen atom to which they are attached do not form an optionally substituted saturated heterocyclic ring of 3 to 8 atoms when $R_1$ and $R_3$ are hydrogen, $R_2$ is hydrogen, $C_1$–$C_6$ alkyl, phenyl, benzyl, 4-chlorophenylmethyl, 4-nitrophenylmethyl, or 4-aminophenylmethyl and $R_3$ is hydrogen, methyl, isopropyl, isobutyl or benzyl; and (b) $R_5$ is not 2-pyridyl or 2-thiazolyl when $R_1$, $R_3$ and $R_6$ are hydrogen, $R_2$ is n-pentyl and $R_4$ is isopropyl; and (c) $R_5$ and $R_6$ are not both ethyl when $R_1$ and $R_3$ are hydrogen, $R_2$ is n-pentyl and $R_4$ is methyl or isopropyl.

2. The method of claim 1 wherein $R_1$ represents hydrogen, or $C_1$–$C_6$ alkyl; $R_3$ represents hydrogen or $C_1$–$C_6$ alkyl; $R_4$ represents the side chain of a natural or non-natural alpha amino acid; $R_5$ and $R_6$ independently represent hydrogen, $C_1$–$C_6$ alkyl, or cycloalkyl or $R_5$ and $R_6$ taken together with the nitrogen atom to which they are attached form an optionally substituted saturated heterocyclic ring of 3 to 8 atoms; and $R_7$ represents hydrogen or an acyl group.

3. The method of claim 1 wherein $R_1$ is hydrogen or methyl.

4. The method of claim 1 wherein $R_2$ is:

$C_1$–$C_6$ alkyl, $C_3$–$C_6$ alkenyl or $C_3$–$C_6$ alkynyl; phenyl ($C_1$–$C_6$ alkyl)-, phenyl ($C_3$–$C_6$ alkenyl)- or phenyl ($C_3$–$C_6$ alkynyl)- optionally substituted in the phenyl ring; cycloalkyl ($C_1$–$C_6$ alkyl)-, cycloalkyl ($C_3$–$C_6$ alkenyl)- or cycloalkyl ($C_3$–$C_6$ alkynyl)- optionally substituted in the cycloalkyl ring; heterocyclyl ($C_1$–$C_6$ alkyl)-, heterocyclyl ($C_3$–$C_6$ alkenyl)- or heterocyclyl ($C_3$–$C_6$ alkynyl)- optionally substituted in the heterocyclyl ring.

5. The method of claim 1 wherein $R_2$ is methyl, ethyl, n-propyl, n-butyl, n-pentyl, n-hexyl, 2-methoxyethyl, prop-2-yn-1-yl, 3-phenylprop-2-yn-1-yl, 3-(2-chlorophenyl)prop-2-yn-1-yl, but-2-yn-1-yl, cyclopentylmethyl, cyclopentylethyl, cyclopentylpropyl, phenylpropyl, 4-chlorophenylpropyl, 4-methylphenylpropyl, or 4-methoxyphenylpropyl.

6. The method of claim 1 wherein $R_2$ is n-butyl, benzyl or cyclopentylmethyl.

7. The method of claim 1 wherein $R_3$ is hydrogen or methyl.

8. The method of claim 1 wherein $R_4$ is:

a group- $(Alk)_n R_9$ where Alk is a $C_1$–$C_6$ alkyl or $C_2$–$C_6$ alkenyl group optionally interrupted by one or more —O—, or —S— atoms or —N($R_{12}$)— groups where $R_{12}$ is a hydrogen atom or a $C_1$–$C_6$ alkyl group, n is 0 or 1, and $R_9$ is an optionally substituted cycloalkyl or cycloalkenyl group; or a benzyl group substituted in the phenyl ring by a group of formula $OCH_2COR_8$ where $R_8$ is hydroxyl, amino, $C_1$–$C_6$ alkoxy, phenyl ($C_1$–$C_6$) alkoxy, $C_1$–$C_6$ alkylamino, di($C_1$–$C_6$ alkyl)amino, (phenyl($C_1$–$C_6$ alkyl))amino, or a heterocyclic ($C_1$–$C_6$) alkyl group, either being unsubstituted or mono-or disubstituted in the heterocyclic ring with halo, nitro, carboxy, $C_1$–$C_6$ alkoxy, cyano, $C_1$–$C_6$ alkanoyl, trifluoromethyl, $C_1$–$C_6$ alkyl, hydroxy, formyl, amino, $C_1$–$C_6$ alkylamino, di-($C_1$–$C_6$ alkyl) amino, mercapto, $C_1$–$C_6$ alkylthio, hydroxy($C_1$–$C_6$ alkyl), mercapto($C_1$–$C_6$ alkyl), or ($C_1$–$C_6$) alkylphenylmethyl; or a group —$CR_a R_b R_c$ in which:

each of $R_a$, $R_b$ and $R_c$ is independently hydrogen, $C_1$–$C_6$ alkyl, $C_2$–$C_6$ alkenyl, $C_2$–$C_6$ alkynyl, phenyl ($C_1$–$C_6$) alkyl, ($C_3$–$C_8$) cycloalkyl; or $R_c$ is hydrogen and $R_a$ and $R_b$ are independently phenyl or heteroaryl; or $R_c$ is hydrogen, $C_1$–$C_6$ alkyl, $C_2$–$C_6$ alkenyl, $C_2$–$C_6$ alkynyl, phenyl ($C_1$–$C_6$ alkyl), or $C_3$–$C_8$ cycloalkyl, and $R_a$ and $R_b$ together with the carbon atom to which they are attached form a 3 to 8 membered cycloalkyl or a 5-to 6-membered heterocyclic ring; or $R_a$, $R_b$ and $R_c$ together with the carbon atom to which they are attached form a tricyclic ring; or $R_a$ and $R_b$ are each independently $C_1$–$C_6$ alkyl, $C_2$–$C_6$ alkenyl, $C_2$–$C_6$ alkynyl, phenyl ($C_1$–$C_6$ alkyl), or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —$CO_2H$, $C_1$–$C_4$ perfluoroalkyl, —$CH_2OH$, —$CO_2(C_1$–$C_6$alkyl), —O($C_1$–$C_6$ alkyl), —O($C_2$–$C_6$ alkenyl), —S($C_1$–$C_6$ alkyl), SO($C_1$–$C_6$ alkyl), $SO_2$ ($C_1$–$C_6$ alkyl), —S($C_2$–$C_6$ alkenyl), —SO($C_2$–$C_6$ alkenyl), —$SO_2(C_2$–$C_6$ alkenyl) or a group-Q-W wherein Q represents a bond or —O—, —S—, —SO—or —$SO_2$— and W represents a phenyl, phenylalkyl, $C_3$–$C_8$ cycloalkyl, $C_3$–$C_8$ cycloalkylalkyl, $C_4$–$C_8$ cycloalkenyl, $C_4$–$C_8$ cycloalkenylalkyl, heteroaryl or heteroarylalkyl group, which group W may optionally be substituted by one or more substituents independently selected from, hydroxyl, halogen, —CN, —$CO_2H$, —$CO_2$ ($C_1$–$C_6$alkyl), —$CONH_2$, —$CONH(C_1$–$C_6$alkyl), —$CONH(C_1$–$C_6$ alkyl)$_2$, —CHO, —$CH_2OH$, $C_1$–$C_4$ perfluoroalkyl, —O($C_1$–$C_6$ alkyl), —S($C_1$–$C_6$ alkyl), —SO($C_1$–$C_6$)alkyl, —$SO_2(C_1$–$C_6$ alkyl), —$NO_2$, —$NH_2$, —NH($C_1$–$C_6$)alkyl, —N($C_1$–$C_6$ alkyl)$_2$, —NHCO($C_1$–$C_6$) alkyl), $C_1$–$C_6$ alkyl, $C_2$–$C_6$ alkenyl, $C_2$–$C_6$ alkynyl, $C_3$–$C_8$ cycloalkyl, $C_4$–$C_8$cycloalkenyl, phenyl or benzyl.

9. The method of claim 1 wherein $R_4$ is phenyl, tert-butyl, isobutyl, benzyl, cyclohexylmethyl, pyridin-3-ylmethyl, tert-butoxymethyl, tert-butyl, 1-benzylthio-1-methylethyl, 1-methylthio-1-methylethyl, or 1-mercapto-1-methylethyl.

10. The method of claim 1 wherein $R_4$ is tert-butyl.

11. The method of claim 1 wherein $R_5$ and $R_6$ are independently hydrogen, methyl, ethyl or cyclohexyl.

12. The method of claim 1 wherein $R_5$ and $R_6$ when taken together with the nitrogen atom to which they are attached form a saturated 5-to 8 membered monocyclic N-heterocyclic ring which is attached via the N atom and which optionally contains $NR_{11}$ wherein $R_{11}$ is hydrogen, $C_1$–$C_6$ alkyl, benzyl, acyl, or an amino protecting group, O, S, SO or $SO_2$ as a ring member, and is optionally substituted on one or more C atoms by hydroxy, $C_1$–$C_6$ alkyl, $C_1$–$C_6$ alkoxy, oxo, ketalised oxo, amino, mono($C_1$–$C_6$ alkyl) amino, di($C_1$–$C_6$ alkyl)amino, carboxy, $C_1$–$C_6$ alkoxycarbonyl, hydroxymethyl, $C_1$–$C_6$ alkoxymethyl, carbamoyl, mono($C_1$–$C_6$ alkyl) carbamoyl, di ($C_1$–$C_6$ alkyl) carbamoyl, or hydroxyimino.

13. The method of claim 1 wherein $R_5$ and $R_6$ when taken together with the nitrogen atom to which they are attached form a substituted or unsubstituted 1-pyrrolidinyl, piperidin-1-yl, 1-piperazinyl, hexahydro-1-pyridazinyl, morpholin-4-yl, tetrahydro-1,4-thiazin-4-yl, tetrahydro-1,4-thiazin-4-yl 1-oxide, tetrahydro-1,4-thiazin-4-yl 1,1-dioxide, thiazolidin-3-yl, hexahydroazipino, or octahydroazocino ring.

14. The method of claim 1 wherein $R_7$ is hydrogen, or a group $R_{20}C(O)$— where $R_{20}$ is a $C_1$–$C_6$ alkyl group.

15. The method of claim 1 wherein $R_7$ is a group $R_2C(O)$— where $R_{20}$ is methyl or ethyl.

16. The method of claim 1 wherein the compound is $N^1$-(1S-dimethylcarbamoyl-2,2-dimethyl-1-propyl)-$N^4$-hydroxy-2R-butyl-succinamide or a pharmaceutically acceptable salt, hydrate or solvate thereof.

\* \* \* \* \*